United States Patent [19]
Zhang et al.

[11] Patent Number: 5,741,773
[45] Date of Patent: Apr. 21, 1998

[54] STORAGE STABLE DENTIFRICE COMPOSITION CONTAINING AN ANTIBACTERIAL CASEIN GLYCOMACROPEPTIDE ADJUVANT

[75] Inventors: Yun Po Zhang, Hillsborough; Abdul Gaffar, Princeton, both of N.J.

[73] Assignee: Colgate Palmolive Company, New York, N.Y.

[21] Appl. No.: 639,871

[22] Filed: Apr. 26, 1996

[51] Int. Cl.$^6$ .................................................. A61K 38/16
[52] U.S. Cl. ............................ 514/8; 514/775; 252/315.6; 424/49; 424/56
[58] Field of Search .................... 514/8, 775; 252/315.6; 424/49, 56

[56] References Cited

U.S. PATENT DOCUMENTS

| 4,391,798 | 7/1983 | Tavss et al. | 424/52 |
| 4,992,420 | 2/1991 | Neeser | 514/8 |
| 4,994,441 | 2/1991 | Neeser | 514/8 |
| 5,416,075 | 5/1995 | Carson et al. | 514/23 |
| 5,624,906 | 4/1997 | Vermeer | 514/23 |

*Primary Examiner*—Cecilia J. Tsang
*Assistant Examiner*—C. Delacroix-Muirheid
*Attorney, Agent, or Firm*—Paul Shapiro

[57] ABSTRACT

Stable oral compositions containing an antibacterial casein glycomacropeptide, an anionic surfactant, and a hydrolyzed protein stabilizer, which stabilizes the casein glycomacropeptide in the presence of the anionic surfactant against inactivation without substantially reducing its antibacterial properties.

26 Claims, No Drawings

STORAGE STABLE DENTIFRICE COMPOSITION CONTAINING AN ANTIBACTERIAL CASEIN GLYCOMACROPEPTIDE ADJUVANT

BACKGROUND OF THE INVENTION

1. Field of the Invention

This invention is directed to a dentifrice composition and more particularly to dentifrice composition containing a casein glycomacropeptide having antiplaque and anticaries activity.

2. The Prior Art

Casein glycomacropeptides have been identified by the art to be effective antibacterial agents against microorganisms responsible for dental plaque and caries. For example, U.S. Pat. Nos. 4,992,420 and 4,994,441 disclose that casein phosphopeptides derived from kappa-casein are effective for inhibiting the growth of *streptococcus mutans*, a bacteria species associated with dental caries and plaque formation.

Because of its antibacterial effectiveness, it is desirable to formulate oral compositions such as toothpastes, gels or mouthrinses by which the casein glycomacropeptide can be conveniently delivered to oral tissue. However, in efforts to utilize such casein glycomacropeptides in dental products suitable for home use, the casein glycomacropeptides have been found to be incompatible with anionic surfactants such as sodium lauryl sulfate conventionally used to prepare dentifrice compositions such as toothpastes and gels, the casein glycomacropeptide being biologically inactivated by the surfactant.

There is therefore a clear need in the art to prepare oral care products utilizing a casein glycomacropeptide wherein ingredients such as surfactants used to prepare the oral care product do not interact or otherwise inactivate the casein glycomacropeptide present in the composition so that optimum antibacterial efficacy of the glycomacropeptide is available when the composition is applied to oral tissue.

SUMMARY OF THE INVENTION

In accordance with the present invention there is provided an oral care composition wherein casein glycomacropeptide compounds incorporated therein encounter minimal biological inactivation and provide excellent antiplaque and anticaries performance, such composition comprising an aqueous vehicle having incorporated therein a casein glycomacropeptide, an anionic surfactant and an amount of a hydrolyzed protein compound effective to reduce or prevent the biological inactivation of the casein glycomacropeptide.

Oral compositions containing the casein glycomacropeptide and the hydrolyzed protein compound are efficacious with respect to plaque and caries control without compromising the rheological and foaming characteristics of the composition.

DESCRIPTION OF THE PREFERRED EMBODIMENTS

Casein glycomacropeptide compounds useful in the practice of the present invention include those identified in U.S. Pat. No. 4,992,420 as kappa-caseino glycomacropeptides and desialylated derivatives thereof.

The term "kappa-caseino glycopeptides" includes within its meaning a caseino glycopeptide, which is the water soluble component emanating from the hydrolysis of kappa-casein by rennet, and a caseino-glycopeptide obtained by proteolysis of caseino-macroglycopeptide. Desialylated derivatives are obtained from caseino glycopeptides by more or less complete elimination of the sialic acids, i.e. N-acetylneuraminic and N-glycollylneuraminic acids, from the oligosaccharide chains of the caseino glycopeptide.

The preparation of kappa-caseino-glycopeptides is more fully disclosed in U.S. Pat. No. 4,992,420, the disclosure of which is herein incorporated by reference. Other casein glycomacropeptide compounds useful in the practice of the present invention are the kappa-caseino glycomacropeptides disclosed in U.S. Pat. No. 5,075,424, the disclosure of which is also incorporated herein by reference.

The casein glycomacropeptide is incorporated in the oral composition of the present invention at a concentration of about 0.5 to abut 10% by weight, and preferably at about 3.0 to about 8% by weight.

Hydrolyzed protein compounds useful to preserve the antibacterial activity of the casein glycomacropeptides in accordance with the practice of the present invention include hydrolyzed collagen proteins, specifically positively charged hydrolyzates containing high concentrations of basic amino acids obtained by extraction from a partially hydrolyzed collagen faction and isolation by ion exchange treatment with an anion exchange resin or a partially charged hydrolyzed collagen protein. Such hydrolyzed collagen proteins are known to the art and are more fully described in U.S. Pat. No. 4,391,798, the disclosure of which is herein incorporated by reference. Other useful hydrolyzed proteins include gelatin, obtained by boiling animal parts such as skin, tendons and ligaments and such other proteinaceous compounds as polylysine, polyarginine and protamine sulfate, polyvinyl pyridinium ammonium salts and poly N-(2hydroxypropyl methacrylamide.

Hydrolyzed collagen protein compounds are preferred for use as stabilizers of casein glycomacropeptide antibacterial activity. Commercially available hydrolyzed collagen proteins include Crotein Q®, a quaternary derivative of hydrolyzed collagen protein available commercially from Croda Inc., New York, N.Y. Crotein Q has a minimum pI of 9.5–10.5, is an off-white, free flowing powder and its adopted name is steartrimonium hydrolyzed animal protein. The free amino groups in the protein molecule react with a quaternary ammonium reactant to form the quaternized derivative which has multiple positive changes. As shown diagrammatically below, at pH's below 5.5, Crotein Q will exhibit a double positive charge, due to protonation of NH groups in the protein chain. At pH 9.5, the quaternary group of Crotein Q remains positively charged.

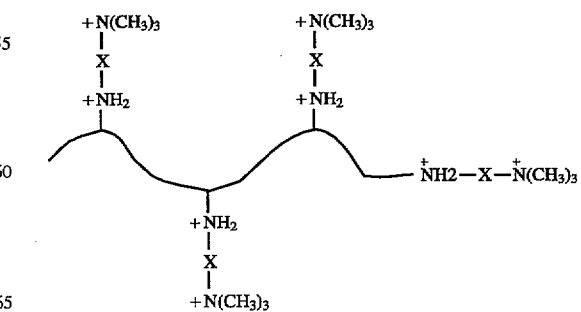

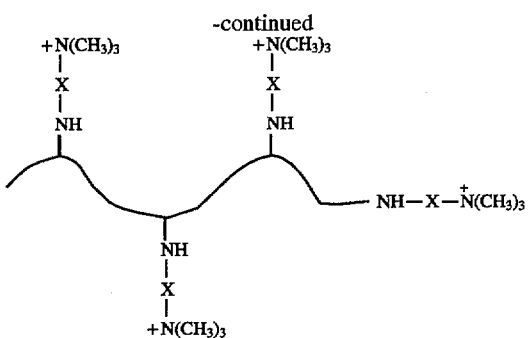

Another example of a commercially available hydrolyzed collagen protein is gelatin (food grade) available from American Gelatin Company, a regular hydrolyzed collagen protein prepared by boiling animal parts such as skin, tendons, ligaments and bones with water. Above pH 5.5, the gelatin product is uncharged. At pH's below 5.5, gelatin (type B) exhibits a positive charge, due to protonation of NH groups in the protein chain, as shown diagrammatically below:

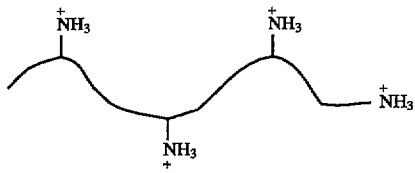

The use of about 0.1 to about 2.5% by weight of the hydrolyzed protein compound in the preparation of the composition of the present invention is sufficient to inhibit any inactivating effect on the antibacterial efficacy of the casein glycomacropeptide occasioned by the presence of an anionic surfactant in the composition.

To prepare a dentifrice composition such as a toothpaste or gel, abrasives including conventional dentifrice abrasives, such as finely divided silica, hydrated alumina, calcium carbonate, sodium bicarbonate and dicalcium phosphate (anhydrous and/or dihydrate) are incorporated in the composition at a concentration of about 10 to about 30% by weight based on the composition and preferably at a concentration of about 15 to about 25% by weight. At these abrasive levels, the vehicle is comprised of about 25 to about 40% by weight water as well as a humectant such as glycerol, sorbitol, propylene glycol or mixtures thereof at a concentration of about 25 to about 45% by weight and preferably about 25 to about 35% by weight of the composition.

Thickeners or gelling agents are used in the preparation of the dentifrices of the present invention and include silica thickeners, carboxymethyl cellulose, sodium carboxymethyl cellulose, carob bean gum, iota carrageenan, gum tragacanth, hydroxymethyl cellulose, hydroxyethyl cellulose, hydroxypropyl cellulose, and alginates and are incorporated in the oral compositions at concentrations from about 0.2 to about 3.0% by weight.

Surfactants which may be included in the composition of the present invention include anionic surfactants such as the water soluble salts of the higher alkyl sulfates or sulfoacetate, such as sodium lauryl sulfate, sodium lauryl sulfoacetate or other suitable alkyl sulfate or sulfoacetate having 8 to 18 carbon atoms in the alkyl group; water soluble salts of sulfonated monoglycerides of higher fatty acids, such as sodium coconut monoglyceride sulfonate or other suitable sulfonated monoglyceride of a fatty acid of 10 to 18 carbon atoms; sodium lauryl phosphate salts of amides of higher fatty acid, e.g., 12 to 16 carbon atom acids, with lower aliphatic amino acids, e.g., taurine or sarcosine, or other amino acid of 2 to 6 carbon atoms, such as sodium-N-methyl-N-palmitoyl tauride, sodium N-lauroyl-, N-myristoyl- and N-palmitoyl sarcosinates; water soluble salts of the esters of such fatty acids with isethionic acid or with glycerol monosulfate, such as the sodium salt of monosulfated monoglyceride of hydrogenated coconut oil fatty acids; water soluble salts of olefin sulfonates, e.g., alkene sulfonates or hydroxyalkene sulfonates or mixtures thereof having 12 to 16 carbon atoms in the carbon chain of the molecule; and water soluble soaps of higher fatty acids, such as those of 12 to 18 carbon atoms, e.g., coconut fatty acids.

Surfactants are included in the composition of the present invention at a concentration of about 0.5 to about 3.0% by weight and preferably about 1.0 to about 2.5 % weight.

Various other materials may be incorporated into the dentifrice preparations of the present invention such as flavoring agents, sweetening agents and coloring materials such as dyes and pigments which are incorporated in the dentifrice compositions of the present invention in amounts which do not adversely affect the properties and characteristics desired in the dentifrice components.

Any suitable flavoring or sweetening materials may be employed in formulating a flavor for the oral composition of the present invention. Examples of suitable flavoring constituents include flavoring oils, for example, oils of spearmint, peppermint, wintergreen, sassafras, clove, sage, as well as methyl salicylate. Suitable sweetening agents include lactose, maltose, sodium cyclamate and saccharine. Suitably, flavor and sweetening agents together comprise from about 0.01 to 5% or more of the composition. Preferably, the amount of flavoring oil is about 0.5 to about 2.0% by weight and the sweetening agent is from 0.1 to 4 or 0.1 to 0.5% by weight (the latter range being for artificial sweeteners, such as saccharine).

Pigments such as $TiO_2$ and coloring materials which are generally commercially available food dye solutions which are inert with respect to the other ingredients of the oral composition are included at a concentration of about 0.05 to about 2.0% by weight.

In the preparation of dentifrices such as toothpastes and gels, a premix in water is formed in which the water soluble ingredients are first dissolved followed by the water insoluble ingredients, if any. If desired, the lipophilic components may be premixed together and such premix can be mixed with the hydrophiles premix, after which the water insoluble particulate materials may then be blended. The pH of the dentifrice is maintained at a neutral pH and preferably a pH of between 6.7 and 7.2. For example, the thickener is dispersed with water and humectants. The surfactant, hydrolyzed protein compound, casein glycomacropeptide, abrasive, sweetener, flavor and colorant are then separately added and uniformly dispersed. The dentifrice is then thoroughly deaerated (e.g., in vacuo) and packaged. The addition and mixing of the ingredients is conducted in a low humidity environment and preferably under a vacuum of 20–30 inches and preferably 28–30 inches mercury.

In addition to dentifrices such as toothpaste or gel compositions for oral application containing the hydrolyzed protein compound and casein glycomacropeptide, the oral composition of the present invention may be in any other convenient form, such as a mouthrinse, spray, tablet, lozenge, tooth powder, chewing gum.

A typical mouthrinse or spray prepared in accordance with the practice of the present invention contains the following ingredients in percent by weight based on the weight of the mouthrinse or spray composition.

| Ingredients | Wt. % |
|---|---|
| Ethanol (90%) | 5–10 |
| Glycerin | 10–20 |
| Casein Glycomacropeptide | 0.05–10 |
| Anionic Surfactant | 0.1–2.5 |
| Hydrolyzed Protein Stabilizer | 0.1–2.5 |
| Flavor | 0.2–1.5 |
| Sweetener | 0–5 |
| Sodium Benzoate | 0–5 |
| Water | Q.S. |

A typical toothpowder prepared in accordance with the practice of the present invention contains the following ingredients in percent by weight based on the weight of the toothpowder composition.

| Ingredients | Wt. % |
|---|---|
| Abrasive | 70–80 |
| Glycerin | 10 |
| Anionic Surfactant | 0.1–2.5 |
| Sweetener | 0.1 |
| Flavor | 1.0 |
| Casein Glycomacropeptide | 0.05–10 |
| Hydrolyzed Protein Stabilizer | 0.1–2.5 |
| Water | Q.S. |

A typical lozenge formula contains the following ingredients, in percent by weight, based on the weight of the total formulation:

| | % by Weight |
|---|---|
| Humectant | 75–85 |
| Anionic Surfactant | 1–20 |
| Casein Glycomacropeptide | 1–10 |
| Hydrolyzed Protein Slabilizer | 0.1–2.5 |
| Tableting Lubricant | 0.1–5 |
| Sweetener | 0.2–2 |

Suitable humectants include sorbitol and glycerin. Emulsifiers include nonionic polyoxyesters such as polyoxyethylene sorbitan fatty esters e.g. polyoxyethylene 20 sorbitan monolaurate commercially available under the tradenames Polysorbate 20 and Tween 20. Tableting lubricants include magnesium stearate.

Manufacturing of mouthrinses, sprays and dentifrices of the present invention is comparatively simple because, in general, there is little or no criticality in the order of addition of the various ingredients present in such compositions. In the preparation of a mouthrinse or spray the ingredients are dissolved in water and/or alcohol.

A typical chewing gum may contain the following ingredients in the gum formulation:

| Ingredients | % by Weight |
|---|---|
| Gum Base (Natural or synthetic elastomer filler, i.e. gum arabic sorbitol) | 20–30 |
| Sorbitol | 10–20 |
| Casein Glycomacropeptide | 0.05–10 |
| Anionic Surfactant | 0.1–2.5 |
| Hydrolyzed Protein Stabilizer | 0.1–2.5 |
| Flavoring | 0.2–2.0 |
| Dextrose | Q.S. |

Chewing gums and lozenges may be manufactured by procedures normally employed in manufacturing such products, with the casein macroglycopeptide usually preferably being added near the end of the manufacturing process if heat is employed (so as to minimize subjection to elevated temperatures).

The following examples serve to provide further appreciation of the invention but are not meant in any way to restrict the effective scope of the invention. All percentages throughout the specification and claims are by weight % of the final composition unless otherwise indicated and wherein all percentages will total 100% of ingredients in the final composition.

EXAMPLE 1

To determine stabilizing effect of a hydrolyzed protein stabilizer such as Crotein Q or gelatin on a kappa-caseino glycomacropeptide in the presence of an anionic surfactant (sodium lauryl sulfate) in a toothpaste composition, a composition containing these ingredients was prepared by adding thickeners to a pre-mix of water and humectant at a slightly elevated temperature (e.g., from 35° to 60° C.) with proportioning the ingredients to a creamy or gel consistency. Additional ingredients were then added. The resultant toothpaste was then deaerated, flavor was introduced and the toothpaste was packed in tubes. The toothpastes were adjusted a pH of 6.7 with NaOH. The ingredients of the tubed toothpaste compositions are listed in Table I below and identified as Toothpastes 1 and 2. For purposes of comparison, the procedure of Example I was repeated except no hydrolyzed protein stabilizer was included in the toothpaste composition. The composition of the comparative toothpaste identified as Toothpaste 3 which also had a pH of 6.7, is also listed in Table I below.

TABLE I

| Ingredients | Toothpaste 1 Weight (%) | Toothpaste 2 Weight (%) | Toothpaste 3 Weight (%) |
|---|---|---|---|
| Glycerin | 32.000 | 32.000 | 32.000 |
| Carboxymethyl Cellulose | 1.000 | 1.000 | 1.000 |
| Iota Carrageenan | 0.400 | 0.400 | 0.400 |
| Deionized Water | 34.800 | 34.800 | 35.800 |
| Sodium Saccharin | 0.250 | 0.250 | 0.250 |
| Sodium Benzoate | 0.300 | 0.300 | 0.300 |
| Silica Abrasive | 23.000 | 23.000 | 23.000 |
| Sodium Lauryl Sulfate | 1.000 | 1.000 | 1.000 |
| Hydrolyzed Protein Stabilizer | 1.000 (gelatin) | 1.000 (Crotein Q) | — |
| Titanium Dioxide | 0.250 | 0.250 | 0.250 |

TABLE I-continued

| Ingredients | Toothpaste 1 Weight (%) | Toothpaste 2 Weight (%) | Toothpaste 3 Weight (%) |
|---|---|---|---|
| Flavor | 0.750 | 0.750 | 0.750 |
| NaOH (50%) | 0.25 | 0.25 | 0.25 |
| Kappa-Casein | 5.000 | 5.000 | 5.000 |
| Glycomacro-peptide (CGMP) | | | |
| TOTAL | 100.000 | 100.000 | 100.000 |

As the pH of the toothpastes listed in Table I is 6.7, the gelatin stabilizer is uncharged and the Crotein Q stabilizer has a positive charge.

The stabilizing effect of the hydrolyzed protein on the kappa-caseino glycomacropeptide (CGMP) in the presence of the anionic surfactant, sodium lauryl sulfate, was determined by an aging test wherein the tubed toothpastes were exposed to heated air at 40° C. for a 12-week period (which is equivalent to storage at room temperature for a 2-year period) and then determining the amount of the original CGMP remaining in the toothpaste, expressed as "% Recovery". The method used to determine % recovery of CGMP was capillary electrophoresis that made separation and identification by movement in electrical potential (mobility) dependent on size and charge of the tested molecule. The % recovery of CGMP for the aged toothpastes is recorded in Table II below.

TABLE II

| | CGMP Stability @ 40° C. | | | | | | |
|---|---|---|---|---|---|---|---|
| Week | 0 | 2 | 4 | 6 | 8 | 10 | 12 |
| | % Recovery of CGMP after 40° C. Aging | | | | | | |
| Toothpaste 1 | 94 | 92 | 89 | 87 | 90 | 89 | 79 |
| Toothpaste 2 | 93 | 81 | 93 | 80 | 87 | 84 | 72 |
| Toothpaste 3 | 79 | 65 | 48 | 35 | 38 | 36 | 34 |

The results recorded in Table II show the superior aging stability of Toothpastes 1 and 2 containing as the hydrolyzed protein stabilizer gelatin or Crotein Q in a CGMP/anionic surfactant dentifrice in accordance with this invention as compared to an identical toothpaste which did not contain such hydrolyzed protein stabilizer. In the absence of a hydrolyzed protein stabilizer the 12 week aged comparative Toothpaste 3 exhibited a low level of CGMP recovery (34%) believed due to denaturation of CGMP by the artionic surfactant, sodium lauryl sulfate. In the presence, however of either gelatin or Crotein Q or gelatin % recovery of CGMP from 12 week aged Toothpastes 1 and 2 was unexpectedly higher (72–79%) as the stabilizer apparently interacted with the sodium lauryl sulfate surfactant to prevent inactivation of the CGMP.

To determine the effect on CGMP biological activity of the presence of a hydrolyzed protein stabilizer, Toothpaste I containing 5.0% by weight CGMP was diluted with water at a 1:20 weight ratio and used to treat saliva-coated hydroxyapatite (SCHA) beads in accordance with a procedure wherein radio labeled iodine ($125_I$) CGMP was prepared with a commercially-available Bolton-Hunter reagent (ICN Catalog No. 65001), following the procedure set forth in the ICN catalog. The iodine labeled CGMP was separated from the unreacted labeling reagent by size exclusion chromatography on Sephadex G10 in a 0.1 M phosphate buffer containing 0.1% gelatin and 0.1% azide. The SCHA beads were prepared by exposing HPLC grade hydroxyapatite (Bio-Rad Catalog No. 130-0420) to pooled human saliva at 37° C. overnight, and then washing and resuspending in buffer at about 67 mg/ml. A duplicate series of standard CGMP solutions was prepared as serial dilutions of the pure CGMP in a phosphate buffer saturated with magnesium and calcium ions, ranging from about 3400 μg/ml down to 0; similar tubes were prepared with different dilutions of two extracts that had been prepared with CGMP. All tubes then received 0.5 ml of SCHA suspension and 0.05 ml of radio labeled CGMP to about 30,000 dpm.

The tubes were incubated at 37° C. for one hour, then the solid phase was separated by centrifugation and both phases counted. The Toothpaste 1 extract containing CGMP displaced the labeled CGMP from SCHA in the same way as the pure CGMP containing about 2.5 mg/ml of the peptide; comparative Toothpaste 3 failed to displace the labeled CGMP significantly.

The biological activity of CGMP in Toothpaste 1 is recorded in Table III below, biological activity being the % of CGMP measured as being bound to SCHA as casein glycomacropeptides containing kappa-casein have a high affinity (% binding activity) to SCHA due to the hydrophilic residues, e.g. sialic acid attached glycoproteins, in the casein protein. This in vitro test for biological activity had been previously determined to correlate with in vivo antibacterial activity.

For purposes of contrast Toothpaste 3 and Toothpaste C, which was the same as Toothpaste 3 but which did not contain either CGMP or a hydrolyzed protein stabilizer were also tested for binding activity. The binding activity of CGMP in Toothpaste 3 and Toothpaste C is also recorded in Table III below.

As a control, a series of pure CGMP solutions designated solutions A–F were prepared containing varying concentrations of CGMP. The binding activity of the CGMP present in control solutions A–F is also recorded in Table III below.

TABLE III

| Biological Activity of Gelatin Stabitized CGMP Toothpaste | | | |
|---|---|---|---|
| Toothpaste No. | CGMP Concentration (mg/ml) | Stabilizer Concentration (mg/ml) | Relative CGMP Binding (%) |
| 1 | 2.5 | 0.5 | 47.5 |
| 3 | 2.5 | 0 | 20.0 |
| C | 0 | 0 | 3.0 |
| Control Solutions | | | |
| A | 0 | 0 | 3.0 |
| B | 0.25 | 0 | 20.0 |
| C | 0.50 | 0 | 30.0 |
| D | 0.75 | 0 | 40.0 |
| E | 2.0 | 0 | 43.0 |
| F | 3.5 | 0 | 48.0 |

The results recorded in Table III show that when the CGMP concentration in Control solutions A–F was increased, % CGMP binding activity also increased evidencing that binding activity was proportional to the concentration of CGMP present in the solution. The toothpaste extract from the gelatin CGMP toothpaste (Toothpaste 1) provided substantially the same binding activity as the pure CGMP control solutions (Control E–F) of similar concentration indicating that gelatin stabilized CGMP Toothpaste 1 had biological activity equivalent to pure CGMP and had not been inactivated by the other toothpaste ingredients. The toothpaste extract from the comparative CGMIP-containing Toothpaste 3 which did not contain the gelatin stabilizer exhibited substantially reduced binding activity (20%) and the toothpaste extract from Toothpaste C which contained no CGMP (Toothpaste C) did not exhibit any meaningful CGMP binding activity.

What is claimed is:

1. An oral composition comprising in a dental vehicle a casein glycomacropeptide in an amount effective for antibacterial activity, an anionic surfactant and a hydrolyzed protein compound stabilizer in an amount effective to stabilize the antibacterial activity of the casein glycomacropeptide antibacterial activity against inactivation due to the presence of the anionic surfactant.

2. An oral composition according to claim 1, wherein the hydrolyzed protein stabilizer is a hydrolyzed collagen protein.

3. The composition of claim 2 wherein the hydrolyzed collagen protein is a quaternary derivative of hydrolyzed collagen protein.

4. The composition of claim 2 wherein the hydrolyzed collagen protein is food grade gelatin prepared from boiled animal parts.

5. An oral composition according to claim 1, wherein the hydrolyzed protein stabilizer constitutes about 0.1 to 2.5% by weight of the composition.

6. An oral composition according to claim 1, wherein the casein glycomacropeptide constitutes about 0.5 to 10% by weight of the composition.

7. An oral composition according to claim 1, wherein the casein glycomacropeptide is a kappa-caseino glycopeptide and desialylated derivatives thereof.

8. An oral composition according to claim 1, wherein the anionic surfactant is sodium lauryl sulfate.

9. An oral composition according to claim 1, in the form of a toothpaste containing about 30–75% by weight of a water insoluble polishing agent.

10. An oral composition according to claim 1, in the form of a toothpowder containing about 70–80% hydrated alumina.

11. An oral composition according to claim 1, in the form of an aqueous mouthwash containing about 5–10% ethanol.

12. An oral composition according to claim 1, in the form of a chewing gum, comprising about 20–30% of a gum base containing a natural or synthetic elastomer filler.

13. An oral composition according to claim 9 wherein the polishing agent is silica.

14. A method of preparing a storage stable, aqueous oral composition containing a casein glycomacropeptide having anticaries and antiplaque efficacy which stabilized against biological inactivation in the presence of an anionic surfactant, which method comprises adding to an aqueous vehicle a casein glycomacropeptide in an amount effective for antibacterial activity, an anionic surfactant and a hydrolyzed protein compound stabilizer in an amount effective to stabilize the antibacterial activity of the casein glycomacropeptide against inactivation due to the presence of the anionic surfactant and then mixing the glycomacropeptide, hydrolyzed protein and anionic surfactant to obtain the stable composition.

15. The method according to claim 14, wherein the hydrolyzed protein stabilizer is a hydrolyzed collagen protein.

16. The method of claim 15 wherein the hydrolyzed collagen protein is a quaternary derivative of hydrolyzed collagen protein.

17. The method of claim 15 wherein the hydrolyzed collagen protein is food grade gelatin prepared from boiled animal parts.

18. The method of claim 14, wherein the hydrolyzed protein stabilizer constitutes about 0.1 to 2.5% by weight of the composition.

19. The method according to claim 14, wherein the casein glycomacropeptide constitutes about 0.5 to 10% by weight of the composition.

20. The method according to claim 1 wherein the casein glycomacropeptide is a kappa-caseino glycopeptide and desialylated derivative thereof.

21. The method according to claim 14, wherein the anionic surfactant is sodium lauryl sulfate.

22. The method according to claim 14 wherein the composition is in the form of a toothpaste containing about 30–75% by weight of a water insoluble polishing agent.

23. The method according to claim 14, wherein the composition is in the form of a toothpowder containing abut 70–80% hydrated alumina.

24. The method according to claim 14 wherein the composition is in the form of an aqueous mouthwash containing about 5–10% ethanol.

25. The method according to claim 14 wherein the composition is in the form of a chewing gum, comprising about 20–30% of a gum base containing a natural or synthetic elastomer filler.

26. The method according to claim 22, wherein the polishing agent is silica.

* * * * *